United States Patent
Wachtell et al.

(10) Patent No.: US 9,622,683 B2
(45) Date of Patent: Apr. 18, 2017

(54) DEVICE FOR EVACUATING AND/OR MONITORING GAS LEAKING FROM A PATIENT DURING SURGERY OR ANESTHETIZATION

(71) Applicant: FINANCIAL CONSULTANTS LLC, Boise, ID (US)

(72) Inventors: Peter James Wachtell, Boise, ID (US); Kevin Gerard Shea, Boise, ID (US); Owen Francis Shea, San Luis Obispo, CA (US)

(73) Assignee: FINANCIAL CONSULTANTS LLC, Boise, ID (US)

( * ) Notice: Subject to any disclaimer, the term of this patent is extended or adjusted under 35 U.S.C. 154(b) by 0 days.

(21) Appl. No.: 13/940,175

(22) Filed: Jul. 11, 2013

(65) Prior Publication Data
US 2014/0135641 A1     May 15, 2014

Related U.S. Application Data

(60) Provisional application No. 61/670,462, filed on Jul. 11, 2012, provisional application No. 61/776,209, filed on Mar. 11, 2013.

(51) Int. Cl.
*A61M 16/00*     (2006.01)
*A61B 5/08*     (2006.01)
(Continued)

(52) U.S. Cl.
CPC .............. *A61B 5/082* (2013.01); *A61B 5/097* (2013.01); *A61M 16/009* (2013.01);
(Continued)

(58) Field of Classification Search
CPC . A61B 5/0421; A61M 16/04; A61M 16/0434; A61M 16/0461
(Continued)

(56) References Cited

U.S. PATENT DOCUMENTS

| 340,778 A | 4/1886 | Gilbert |
| 2,225,201 A | 12/1940 | Anderson |

(Continued)

FOREIGN PATENT DOCUMENTS

| EP | 0020731 A1 | 1/1981 |
| EP | 2319574 A2 | 5/2011 |

(Continued)

OTHER PUBLICATIONS

Collins Dictionary: Expand.*
(Continued)

*Primary Examiner* — Jacqueline Cheng
*Assistant Examiner* — Puya Agahi
(74) *Attorney, Agent, or Firm* — MH2 Technology Law Group, LLP (57) ABSTRACT

A system is described herein for evacuating gas as it is leaking from a patient's airway. The system comprises a gas evacuation flowpath configured for collecting a gas flow escaping from the patient when inserted into the patient's airway. A vacuum source is connected to the gas evacuation flowpath. Devices that may be employed as part of the system and a method for evacuating gas from a patient are also described.

14 Claims, 9 Drawing Sheets

(51) Int. Cl.
*A61M 16/04* (2006.01)
*A61B 5/097* (2006.01)
*A61M 16/01* (2006.01)
*A61M 16/06* (2006.01)
*A61B 5/00* (2006.01)

(52) U.S. Cl.
CPC ........ *A61M 16/0051* (2013.01); *A61M 16/01* (2013.01); *A61M 16/04* (2013.01); *A61M 16/0434* (2013.01); *A61M 16/0463* (2013.01); *A61M 16/0666* (2013.01); *A61B 5/4211* (2013.01); *A61B 5/4839* (2013.01)

(58) Field of Classification Search
USPC .................. 600/120, 529, 532, 543, 125; 128/207.14–207.17, 200.24, 200.26
See application file for complete search history.

(56) References Cited

U.S. PATENT DOCUMENTS

| | | | |
|---|---|---|---|
| 4,004,585 A | 1/1977 | Boehringer | |
| 4,015,598 A | 4/1977 | Brown | |
| 4,051,847 A | 10/1977 | Henkin | |
| 4,176,666 A | 12/1979 | Hovey | |
| 4,180,066 A | 12/1979 | Boelens et al. | |
| 4,219,020 A | 8/1980 | Czajka | |
| 4,232,667 A | 11/1980 | Chalon et al. | |
| 4,249,528 A | 2/1981 | Mathes | |
| 4,265,239 A | 5/1981 | Fischer, Jr. et al. | |
| 4,312,339 A | 1/1982 | Thompson, Sr. | |
| 4,320,754 A | 3/1982 | Watson et al. | |
| 4,446,864 A * | 5/1984 | Watson et al. | 128/207.14 |
| 4,452,241 A | 6/1984 | Sarnoff et al. | |
| 4,456,008 A | 6/1984 | Clawson et al. | |
| 4,527,558 A | 7/1985 | Hoenig | |
| 4,573,463 A | 3/1986 | Hall | |
| 4,596,246 A | 6/1986 | Lyall | |
| 4,697,593 A * | 10/1987 | Evans et al. | 600/343 |
| 4,807,617 A | 2/1989 | Nesti | |
| 4,848,334 A | 7/1989 | Bellm | |
| 4,934,933 A | 6/1990 | Fuchs | |
| 4,945,906 A * | 8/1990 | Lindkvist | 128/203.29 |
| D314,844 S | 2/1991 | Baharad | |
| 5,005,572 A * | 4/1991 | Raemer et al. | 128/207.14 |
| 5,018,519 A | 5/1991 | Brown et al. | |
| 5,044,363 A | 9/1991 | Burkhart | |
| 5,482,033 A | 1/1996 | Engle et al. | |
| 5,676,133 A | 10/1997 | Hickle et al. | |
| 6,076,524 A * | 6/2000 | Corn | 128/205.12 |
| 6,254,591 B1 * | 7/2001 | Roberson | A61M 16/0463 128/207.14 |
| 7,481,217 B2 | 1/2009 | Milles | |
| 7,596,965 B2 | 10/2009 | Berry et al. | |
| 7,628,034 B2 | 12/2009 | Berry et al. | |
| 7,644,594 B2 | 1/2010 | Berry et al. | |
| 7,669,438 B2 | 3/2010 | Berry et al. | |
| 8,291,905 B2 | 10/2012 | Moenning, Jr. | |
| 8,371,297 B2 | 2/2013 | Carey et al. | |
| 2003/0131853 A1 * | 7/2003 | Wall et al. | 128/207.14 |
| 2003/0145854 A1 | 8/2003 | Hickle | |
| 2006/0076013 A1 | 4/2006 | Berg | |
| 2006/0180156 A1 * | 8/2006 | Baska | 128/207.15 |
| 2007/0137652 A1 * | 6/2007 | Qureshi et al. | 128/207.15 |
| 2007/0221229 A1 * | 9/2007 | Rahaghi et al. | 128/207.14 |
| 2008/0011304 A1 * | 1/2008 | Stewart | 128/207.15 |
| 2008/0078402 A1 * | 4/2008 | Mongeon | 128/207.15 |
| 2008/0105263 A1 * | 5/2008 | Jadhav | A61B 1/267 128/207.15 |
| 2008/0251070 A1 * | 10/2008 | Pinskiy et al. | 128/202.22 |
| 2009/0143996 A1 | 6/2009 | Karlsson et al. | |
| 2009/0235932 A1 | 9/2009 | Nashed | |
| 2010/0024827 A1 * | 2/2010 | Tagliavini | 128/207.14 |
| 2010/0249639 A1 * | 9/2010 | Bhatt | 600/546 |
| 2011/0094508 A1 * | 4/2011 | Carey et al. | 128/203.14 |
| 2011/0139159 A1 * | 6/2011 | Nelson et al. | 128/207.15 |
| 2013/0074840 A1 | 3/2013 | Ahearn et al. | |

FOREIGN PATENT DOCUMENTS

| | | |
|---|---|---|
| WO | 8001044 A1 | 5/1980 |
| WO | 9117794 A1 | 11/1991 |
| WO | 9408650 A1 | 4/1994 |
| WO | 2006124578 A2 | 11/2006 |
| WO | 2008104218 A1 | 9/2008 |
| WO | 2008-144433 | 11/2008 |

OTHER PUBLICATIONS

International Search Report and Written Opinion dated Oct. 18, 2013 from International Application No. PCT/US2013/050154 filed Jul. 11, 2013, pp. 1-11.

* cited by examiner

DEVICE FOR EVACUATING AND/OR MONITORING GAS LEAKING FROM A PATIENT DURING SURGERY OR ANESTHETIZATION

PRIORITY CLAIMS

This present application claims priority benefit to U.S. Provisional Application No. 61/670,462, filed Jul. 11, 2012; and U.S. Provisional Application No. 61/776,209, filed Mar. 11, 2013 the disclosures of both of which are incorporated herein by reference in their entirety.

DETAILED DESCRIPTION

Field of the Disclosure

This invention relates generally to the field of medicine and more specifically to a device for monitoring and evacuating gas that leaks past a seal on an intubation device inserted into a patient during surgery or a patient who is otherwise in need of breathing support.

Background

For patients undergoing surgery, or those that require prolonged respiratory support, inhaled gases (oxygen, nitrogen), and inhalation anesthetic agents are used routinely. These gases are delivered via a closed system, with a goal to retain the inhaled and exhaled gases within the closed system.

The general concept of scavenging anesthetic gases is well known. In anesthetic gas systems that administrate highly toxic gases such as halogenated ethers, it has been known for some time that these substances are harmful. Gas systems have been designed to minimize the exposure of the operating room personnel to these gases. Closed breathing circuits are specifically designed to create a closed system whereby the gas that is breathed in by the patient is subsequently returned via a closed circuit back to the gas administration system. These systems are generally focused on recovering or reusing the anesthetic gases or at least scrubbing them from the air before the air is vented.

One consistent area of leakage of these gases occurs at the interface between the patient's airway and the device delivering the gases. The interface is characterized by an incomplete seal between the patient's tissues and the inserted endotracheal tube or laryngeal mask airway ("LMA").

Leakage of these gases is not without risk, both in the short term and long term. Short term leakage of oxygen is a direct risk to patients, especially in settings where electrical current and electric instruments are present. Oxygen is a fire accelerant, and significant leakage in health care settings can lead to catastrophic fires. These fires can burn the inside of the lungs, as well as other portions of the patient's body. In addition to the risks to the patient, the operating room and other hospital staff are also at risk of burn/inhalation injury.

Long term risks of anesthetic gas leakage are also a concern to hospital operating room and critical care unit staff. Recent research has demonstrated increase concentrations of inhalation anesthetics in operating room staff. The long term exposure risks to these agents have not been clarified in the research literature, but many of these agents have documented tissue toxicity, including neuro-toxicity. Recent research has highlighted these concerns, and raised questions about toxicity with chronic exposure, even at low concentrations.

Current endotracheal tubes ("ETT") and laryngeal mask airway ("LMA") designs (including nasal trumpets for certain difficult cases) often have features that partially address the issue of surgical gas leakage. For example, ETT often use an inflatable cuff to limit leakage from a patient's airway during surgery. While these inflatable cuffs are partially effective, they often do not fully seal, thus resulting in unwanted leakage of the surgical gases from the patient. In addition, the inflation pressure for the inflatable cuff around the airway can cause tissue damage to the windpipe/trachea, if the pressure is inflated to high. Low pressure in the inflatable cuff is less damaging to the windpipe, but it allows for a less secure airway seal.

To provide an improved fit of the seal around the airway and thereby limit leakage, both the ETT and LMA are available in different sizes. However, even properly fitted seals can allow for leakage of surgical gas from a patient's airway. Because of significant anatomic variation seen in the airway and due to the vascular nature of the tissue, obtaining a perfect seal in the majority of cases can be difficult. For this reason, at least small amounts of gas leakage is common.

As mentioned above, a patient's body does not always create a perfect match to a closed breathing circuit and as a result, gas may leak from the breathing circuit from time to time or in some cases continuously. It would be a step forward in the art to provide a means for capturing these gases when and if they leak from a closed breathing circuit within a patient's throat or nares.

SUMMARY

An embodiment of the present disclosure is directed to a system for evacuating gas as it is leaking from a patient's airway. The system comprises a gas evacuation flowpath configured for collecting a gas flow escaping from the patient when inserted into the patient's airway. A vacuum source is connected to the gas evacuation flowpath.

Another embodiment of the present disclosure is directed to a sleeve for use with an intubation device comprising a seal. The sleeve comprises a plug configured to fit above the seal in a patient's airway. A flowpath runs through the plug for evacuating surgical gases. One or more vents are positioned in the plug. The vents are configured so that when a vacuum is applied to the conduit, evacuation of leaking surgical gas from the patient's airway occurs through the conduit.

Still another embodiment of the present disclosure is directed to a device for collecting gas from a patient. The device comprises a conduit comprising a first opening, a second opening and a flowpath between the first and second openings. The conduit is configured to be inserted into the airway of a patient. A flange is positioned proximate the first opening of the conduit. A plurality of vents are positioned in the conduit. The vents are configured to allow gas in a patient's airway to move into the flowpath.

Yet another embodiment of the present disclosure is directed to a method for evacuating gas as it is leaking from a patient's airway. The method comprises collecting a gas that has leaked past a seal of closed circuit gas administration equipment and into the patient's throat or mouth. The collected gas is removed from the patient using a vacuum system.

It is to be understood that both the foregoing general description and the following detailed description are exemplary and explanatory only and are not restrictive of the present teachings, as claimed.

BRIEF DESCRIPTION OF THE DRAWINGS

The accompanying drawings, which are incorporated in and constitute a part of this specification, illustrate embodiments of the present teachings and together with the description, serve to explain the principles of the present teachings.

It should be noted that some details of the figure have been simplified and are drawn to facilitate understanding of the embodiments rather than to maintain strict structural accuracy, detail, and scale.

DESCRIPTION OF THE EMBODIMENTS

Reference will now be made in detail to embodiments of the present teachings, examples of which are illustrated in the accompanying drawings. In the drawings, like reference numerals have been used throughout to designate identical elements. In the following description, reference is made to the accompanying drawing that forms a part thereof, and in which is shown by way of illustration a specific exemplary embodiment in which the present teachings may be practiced. The following description is, therefore, merely exemplary.

An embodiment of the present disclosure is directed to a system for safely capturing surgical gases that have leaked past a seal that is engineered into a patient airway tube, such as an endotracheal tube, laryngeal airway mask, nasal trumpet or nasal tube, or other similar device; and to remove these gases from the patient without allowing them to disperse into the operating room. Oxygen/gas removal can significantly lower the risk for surgical fire and patient burns (e.g., burns in the lungs, airway/mouth, face, neck or shoulders). As an example, the seal can be formed using an inflated cuff, as is well known in the art.

In addition, the system can optionally include the ability to measure the amount of gas leakage that is occurring in real time and to show the operating room staff the current status of the tube seal at any given time. For example, the oxygen that is evacuated by the device may be monitored. Because the concentration ratio of oxygen to anesthetic gases in the leaking surgical gas is a known parameter, the system can use the monitored oxygen to calculate the total amount of leaking surgical gases and thereby provide feedback to the anesthesiologist about the relative volume of any leaks. In a similar manner, the exhaled anesthetic gas concentrations could also be measured to provide an indication of the magnitude of gas leakage while the patient is under anesthesia. One of ordinary skill in the art would readily be able to determine the magnitude of gas leakage given the exhaled anesthetic gas concentrations. Based on this data, the appropriate protocols to prioritize the patient's and the operating room staff's safety can be determined.

Figure 1:
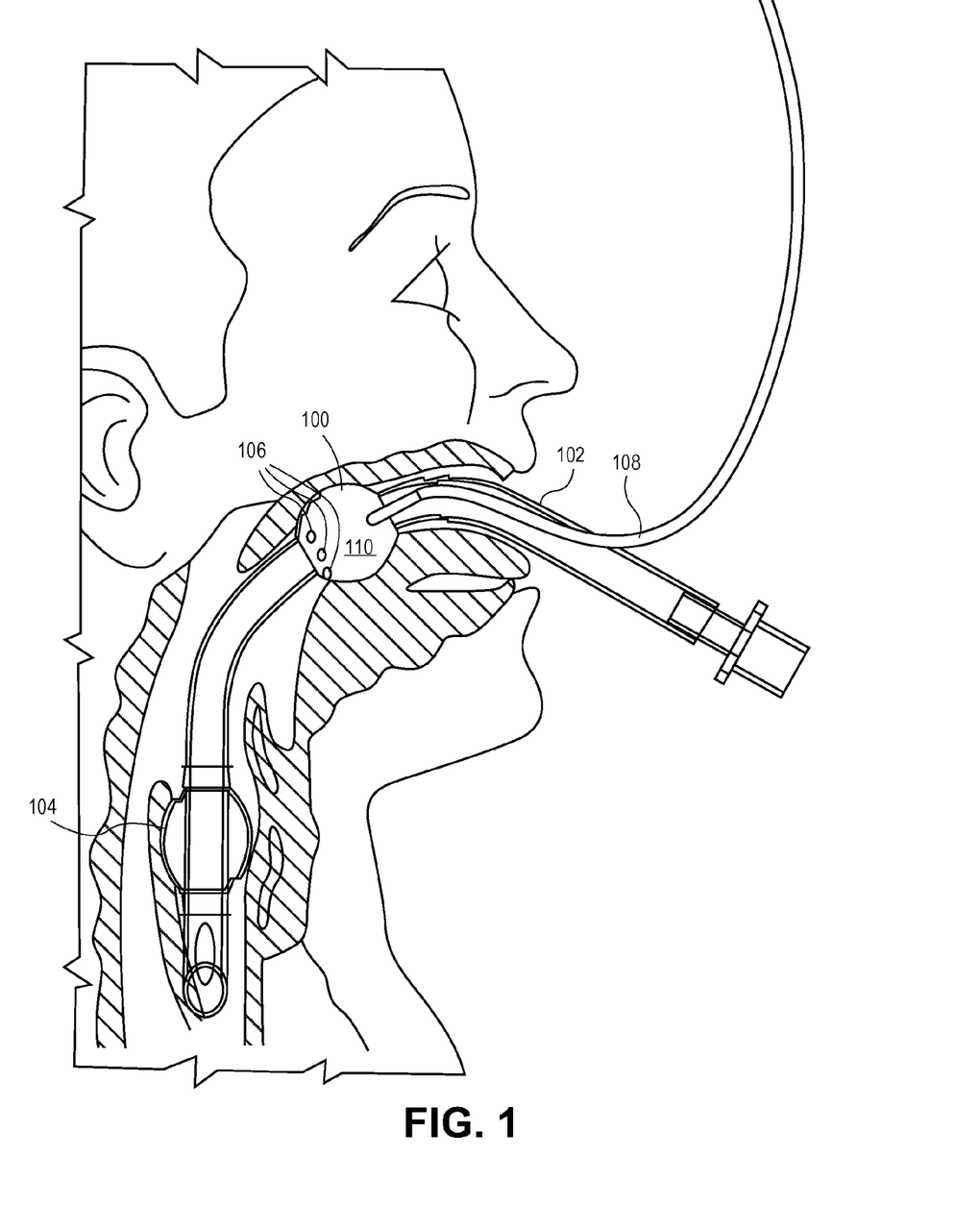
FIG. 1 is a perspective view of a cuffed patient airway tube fitted with a foam evacuation plug inserted into a patient's throat, according to an embodiment of the present disclosure.
Figure 2:
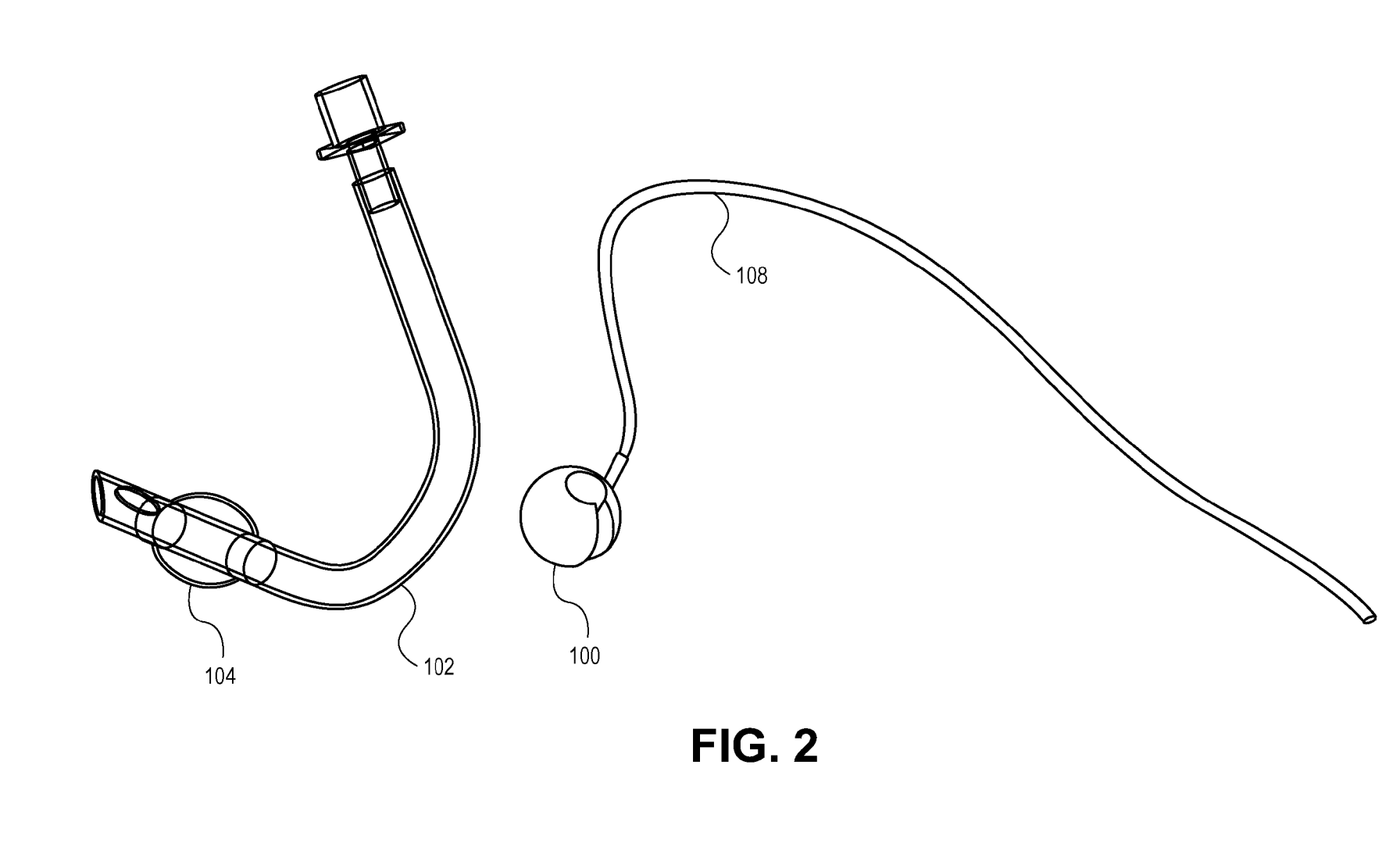
FIG. 2 is an exploded view showing a patient airway tube with a cuff that is commonly used in operating rooms today; and a gas evacuation plug configured to attach to the airway tube, with a vacuum tube affixed thereto, according to an embodiment of the present disclosure.

FIG. 1 illustrates a vented sleeve 100, according to an embodiment of the present disclosure. Sleeve 100 is configured to slip over an existing intubation device 102, which can be an endotracheal tube or laryngeal airway mask. Sleeve 100 fits above a seal 104 of the existing device in the patient's throat or mouth. One or more vents 106 are configured so that when a slight vacuum is applied to the operator end of the sleeve, evacuation of leaking surgical gas from the patient's throat or mouth through the attached conduit 108 results. FIG. 2 provides an exploded view showing patient airway tube 102 with a cuff, or seal 104, which is commonly used in operating rooms today. A sleeve 100 is shown configured to attach to the patient airway tube. A vacuum tube 108 is affixed thereto, according to an embodiment of the present disclosure.

In an embodiment, the sleeve 100 can comprise an expandable plug 110. Expandable plug 110 can comprise any suitable material. In one embodiment, the material is foam, such as an open cell foam, which is capable of expanding to fill the patient's mouth cavity to provide a secondary seal. Alternatively, plug 110 can comprise any other suitable material that can provide the desired secondary seal. In an embodiment, a flow path for evacuating the surgical gases can extend through the plug 110. Conduit 108 can attach to and/or extend through plug 110 as part of the flowpath. Conduit 108 can comprise any suitable material and can be, for example, vacuum tubing.

Figure 3:
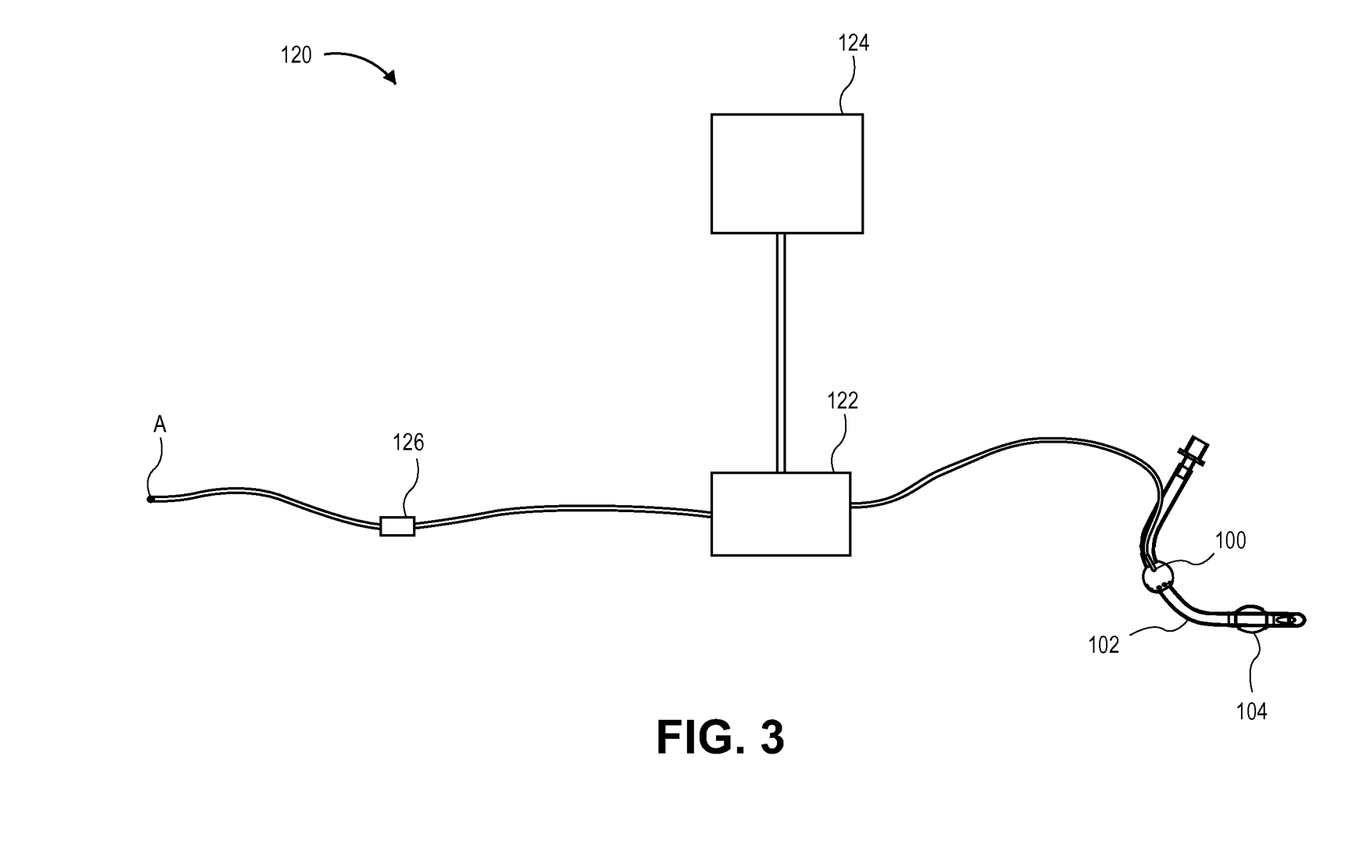
FIG. 3 is a schematic view depicting one potential circuit layout of the device of FIG. 1, in conjunction with oxygen sensors and a gas monitoring device for use in an operating room environment, according to an embodiment of the present disclosure.

FIG. 3 illustrates a system 120 for monitoring gases in an operating room environment, according to an embodiment of the present disclosure. The system 120 comprises a patient airway tube 102 having a seal 104. A sleeve 100 is attached to tube 102. In an embodiment, the tube 102 and sleeve 100 can be those described above in connection with FIGS. 1 and 2.

One or more sensors 122 are fluidly connected to the sleeve 100. The one or more sensors are capable of real time, continuous monitoring of a gas that is drawn from a patient using the sleeve 100. In an embodiment, the gas being sensed can be chosen from oxygen gas, $CO_2$ or anesthesia. Gas sensors 122 can also be used to determine pH of the gas evacuated from the patient.

The sensed gas levels coming from the patient can be compared to, for example, ambient levels of gases, such as $CO_2$ or oxygen, in the operating room. For example, sensors 122 can be kept in a container that is separate from the ambient operating room atmosphere. Gas that is drawn from the patient can be compared to the ambient levels of oxygen in the operating room. If sensors 122 indicate higher oxygen concentrations in the gas drawn from the patient relative to the ambient levels, this would be indicative to the operator that a leak of surgical gases is occurring. Alternatively, in an embodiment employing a sensor that measures anesthetic gases directly, the sensor can provide a direct indication of any gas leakage without the need for comparison with ambient oxygen levels.

A gas monitoring device 124 can be in communication with the one or more sensors 122. Gas monitoring device 124 can include a component chosen from, for example, a data logger, alarm system or monitoring screen.

A vacuum pressure valve 126 is employed to provide a steady and suitably low level of vacuum pressure to the gas evacuation plug while it is placed inside the patient's throat or oral cavity. Vacuum pressure valve 126 can be connected to the operating rooms vacuum evacuation facility at, for example, point "A".

As discussed above, the ability to provide a slight vacuum sufficient to evacuate a leaking surgical gas above a primary seal can allow the system to flow the leaking gas past an oxygen sensor, such as, for example, a sensor that is placed along the evacuation line itself. Because surgical gases comprise at least some oxygen, the system can be used to determine when the surgical gases are being leaked from the patient. For example, by measuring the concentration of oxygen in the gas and correlating it to the level of oxygen that is being used for that patient, the operator can monitor the relative amount of gas that is leaking from the patient at any given time. In an embodiment, this data can be provided to the operator in the form of a screen charting the trend line of the oxygen concentration of the gas that is being evacuated relative to the oxygen concentration in the operating room itself. In a similar manner, monitoring the concentrations of leaked anesthetic gases can also be used to determine the magnitude of the gas leak.

Charting this trend line can aid in several different aspects of the operating room's case management. Large volumes of enriched oxygen leaking into the operating room can be hazardous with regard to creating a fire hazard or an environment where flash fires can occur. This is both dangerous for patients and for operating room personnel. Being informed of leaking oxygen can serve to allow the anesthesiologist to limit the amount of gas escaping into the operating room and/or to take steps to prevent the buildup of such gases to dangerous levels.

As part of this process, the identification of a leak around the cuff of an endotracheal tube or other such device allows the operator to slightly increase the pressure on the inflatable cuff such that the minimum amount of inflation can be used to create an effective seal. This is an improvement over current practice, in that too much cuff inflation can cause harm to the patient's vocal cords and airway tissue, and discomfort to the patient. By determining the amount of pressure that can be employed to maintain an effective seal, an operator using this system would be able to accurately and continuously monitor the amount of pressure that is being used to inflate the cuff to insure the minimal level of patient discomfort or harm.

The system can also include the ability to notify the operating room personnel about anesthesia gas leakage by detecting the presence of increased concentration of $CO_2$ from the gas that leaks. Ambient levels of $CO_2$ gas are approximately 0.03% while $CO_2$ in exhaled breath is approximately 4%. Due to the higher relative concentration of $CO_2$ in exhaled breath, monitoring of the $CO_2$ gas concentration in the evacuated gas stream coming from the patient can inform the anesthesiologist if exhaled breath is leaking from around the seal on the patient airway tube. The monitoring of $CO_2$ can indicate a leak even when enriched oxygen is not being used during the surgery.

In addition to monitoring gas concentrations, the devices of the present disclosure can optionally include the ability to measure the pH level and/or to determine if acid is refluxing from the stomach into the airway region. The pH level or change thereof can be used to warn the surgical team of potential danger to the patient's airway. Sensing the pH can be performed in any desired manner. In an embodiment, gases collected from the patient can be analyzed to determine pH or changes in pH, which may be used to indicate reflux in the patient's airway. Devices for sensing pH levels of a gas flow are well known in the art. In another embodiment, the devices of the present disclosure can include a small probe (not shown) that sits near the airway. Any suitable pH probe can be employed. Suitable pH probes are well known and one of ordinary skill would readily be able to employ such probes, such as by positioning a pH probe on any of the airway devices of the present disclosure. If fluid comprising acidic contents from the patient's stomach comes into the region near the airway, the probe can identify a drop in pH. Regardless of the technique used to detect pH, the change in pH can be communicated to the operating team to make them aware of a potentially dangerous environment for the patient's airway. If these conditions are identified, an anesthesiologist can act appropriately, such as by removing the potentially harmful fluid from near the airway and/or by modifying the anesthesia technique appropriately to protect the patient.

Figure 4:
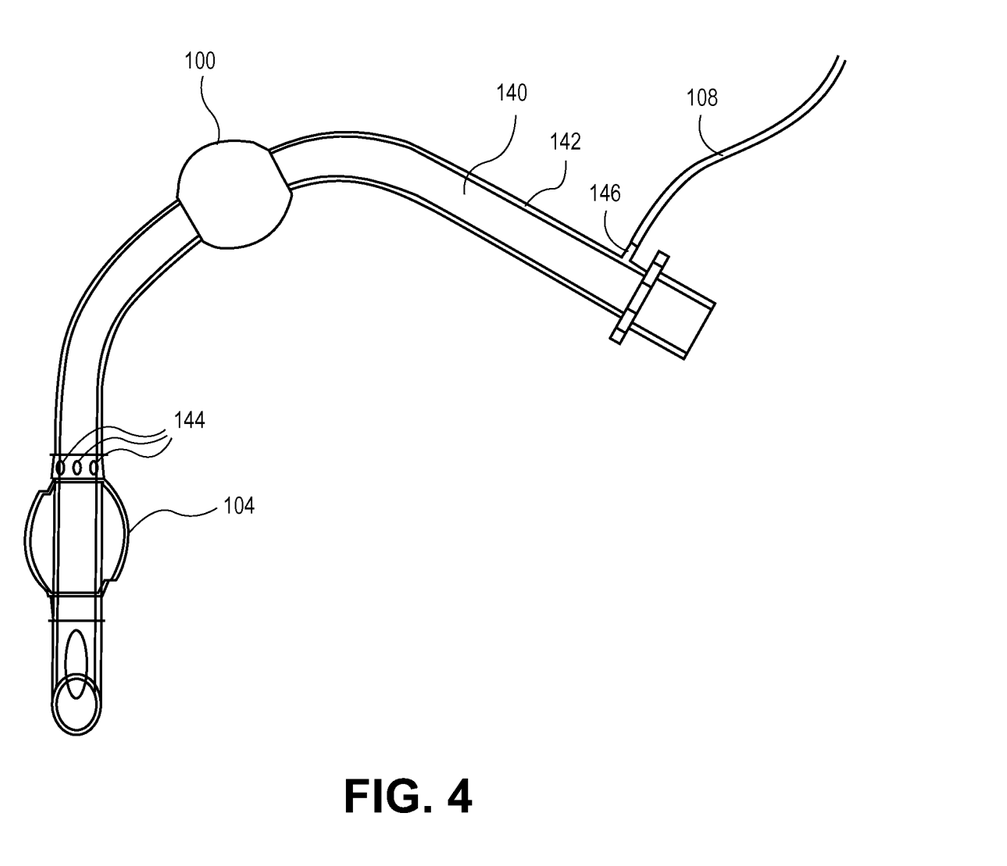
FIG. 4 illustrates a multi-lumen device, according to an embodiment of the present disclosure.

FIG. 4 illustrates an intubation device comprising a fully integrated flowpath for evacuating leaking gases, according to an embodiment of the present disclosure. For example, the intubation device can be in the form of an endotracheal tube comprising a multi-lumen conduit. As illustrated in FIG. 4, an endotracheal tube can include a large lumen 140 that serves to deliver anesthetic gases into and out of the lungs of the patients, while one or more smaller lumens 142 are dedicated to providing vacuum pressure to evacuate any gasses that have leaked above the tube seal 104. Vents 144 provide fluid communication between the patient's airway above the seal 104 and the small lumen 142, thereby allowing leaking gas to flow into the small lumen 142 and out of the patient. Vacuum pressure can be provided by any suitable means, such as through conduit 108 attached to a port 146 in the multi-lumen conduit. The multi-lumen conduit can be made of any suitable material, such as, for example, PVC. The smaller lumen 142 can be in the form of a concentric annulus or any other suitable conduit configuration.

In an alternative embodiment, it may be possible to evacuate leaking gases without a secondary seal device. For example, in the embodiment of FIG. 4, sleeve 100 may be eliminated. Leaking gases can be collected by simply providing a sufficient vacuum through the one or more vents 144.

Figure 5:
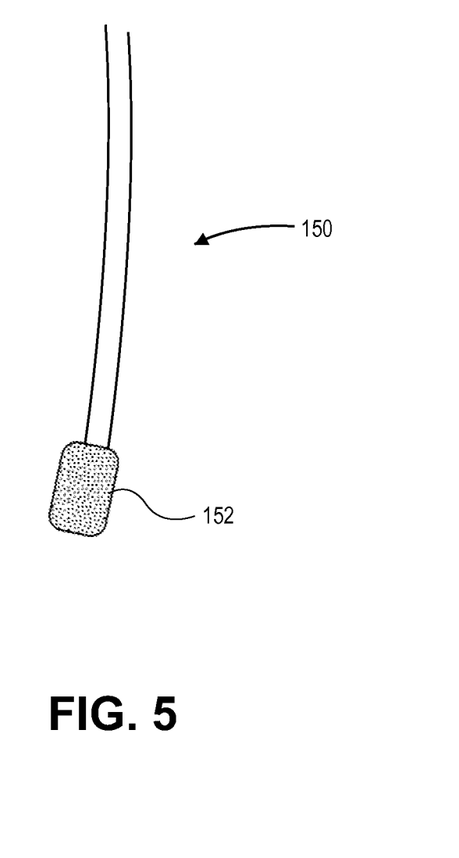
FIG. 5 is a perspective view of a separate tube that can be placed in a patient's airway in addition to and/or adjacent to an intubation device for providing surgical gas to a patient, such as an endotracheal tube, a laryngeal mask airway tube, or a nasal device, according to an embodiment of the present disclosure.

FIG. 5 illustrates a tubular device 150 that can be placed either through the patient's mouth or nares separately or together with an existing device 102 for providing surgical gases to a patient, according to an embodiment of the present disclosure. The tubular device 150 can include a cap or spacer positioned at or near the end of a tube. For example, the end of the tube can be fitted with a foam evacuation plug 152. The foam plug 152 can reduce the likelihood of developing an area of higher pressure suction that might damage the mucosal tissue. The tubular device can be placed in the patient's airway in addition to and/or adjacent to, for example, an endotracheal tube, a laryngeal mask airway tube, or a nasal airway tube.

The tubular device 150 allows for evacuating and/or monitoring surgical gases, such as oxygen and anesthetic gases that have leaked past a seal on an endotracheal tube, laryngeal mask airway tube, nasal device or other device for delivering oxygen and other gases to patients. A means can be employed for applying a vacuum to the tubular device 150 such that any oxygen or accompanying anesthetic gases that leak from around the seal are drawn from the patient and evacuated from the operating room, similarly as described for sleeve 100 and the system of FIG. 3. In an embodiment, tubular device 150 can replace sleeve 100 in the system of FIG. 3.

Figure 6:
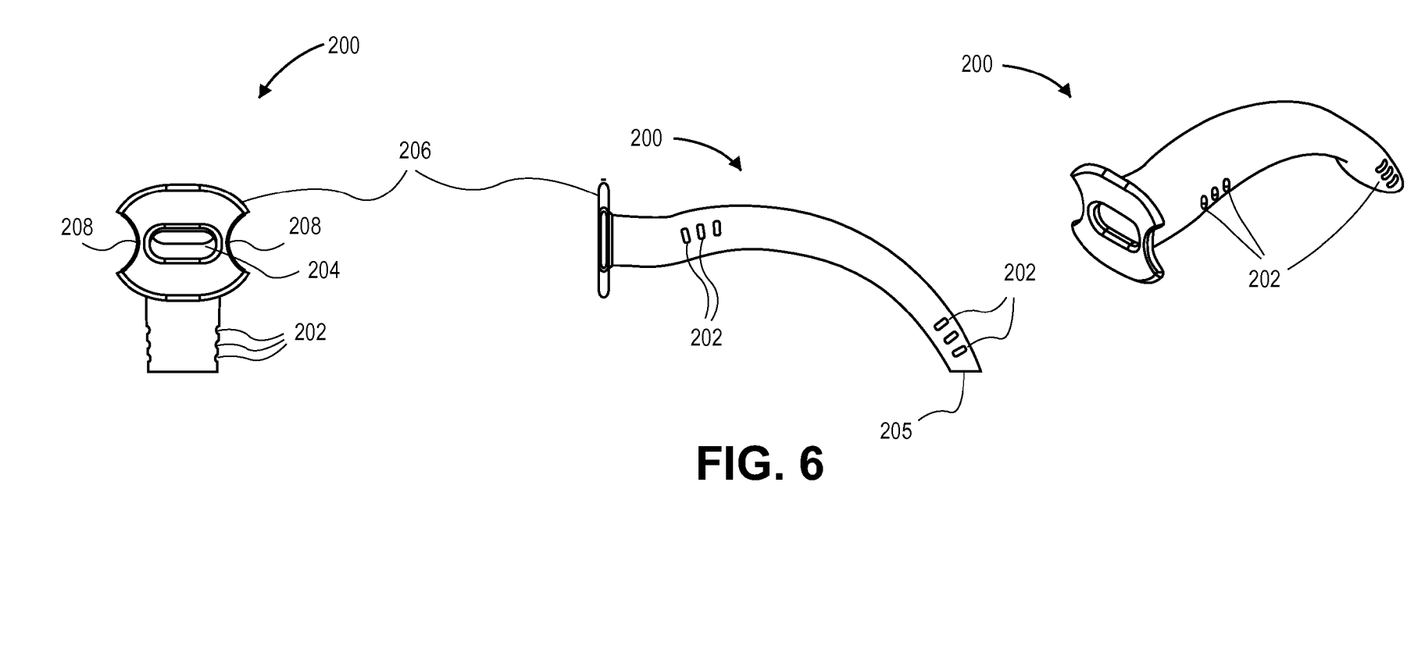
FIGS. 6 and 7 illustrate Guedel airways that can be employed as a gas evacuation device, according to an embodiment of the present disclosure.
Figure 7:
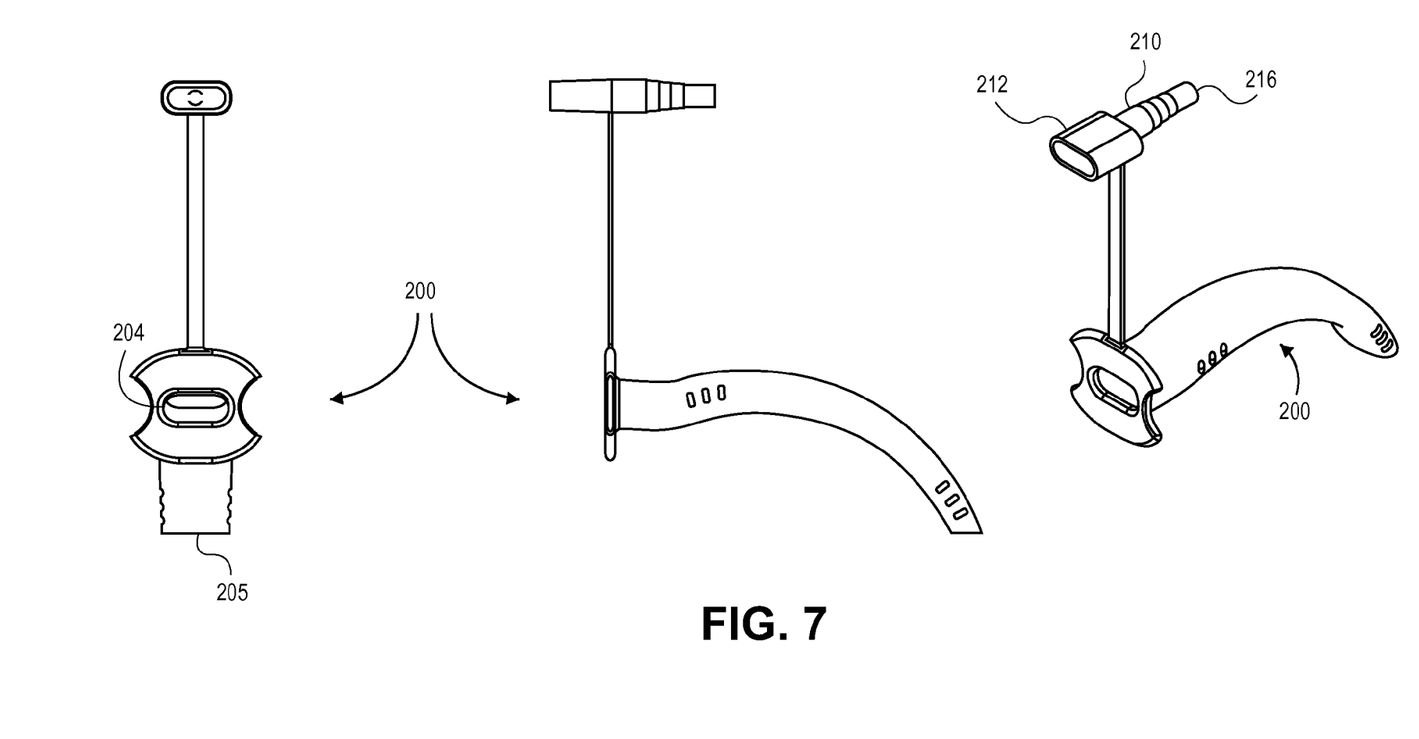
Figure 8:
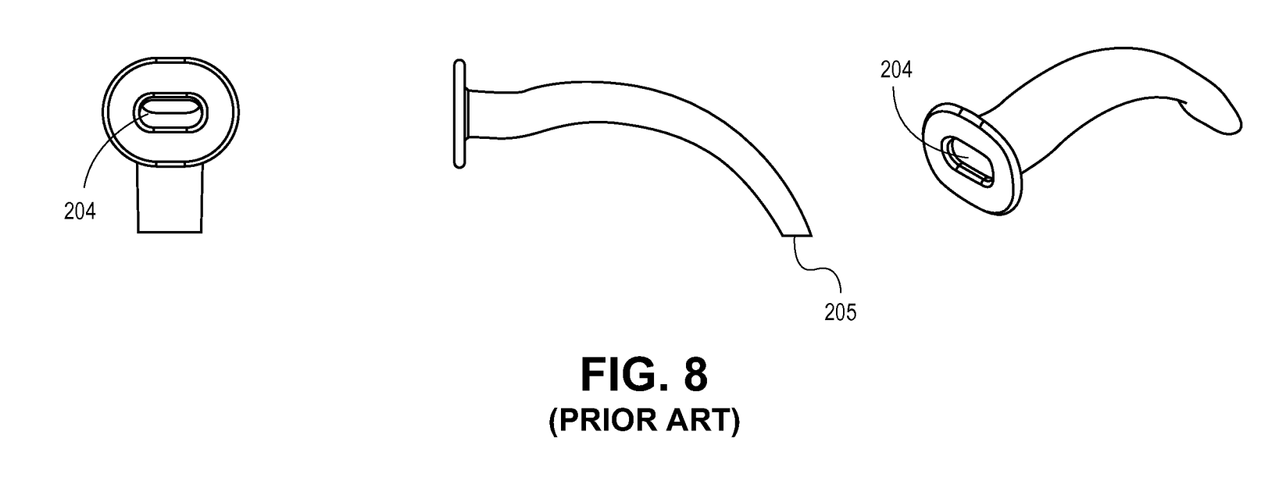
FIG. 8 is a diagram of a standard Guedel Airway.

FIGS. 6 and 7 illustrate a Guedel airway design that can be used to evacuate or scavenge gas as it is leaking from a patient's throat. Geudel airways are generally well known in the art. A conventional Geudel airway is shown in FIG. 8. However, the Guedel airway 200, as shown in FIGS. 6 and 7, has been modified so that it can functionally replace the device of FIG. 1 in the system of FIG. 3. In an embodiment, the Guedel airway designs do not include a sleeve 100.

Guedel airway 200 includes vents 202 in the airway. Vents 202 are configured to allow gas in the patient's throat to move into the modified Guedel airway. Employing a plurality of vents 202 can provide redundant access to the airway from the patient's throat area in order to decrease the likelihood that tissue can be sucked up against a single vent opening when suction is applied to the airway and thereby clog the airway. If only a single opening 205 exists (as in the conventional airway of FIG. 8) the opening 205 can potentially be suctioned up against soft tissue in a patient's throat area and become occluded.

A flange 206 is positioned at an end of the Geudel airway. Flange 206 can be designed with notches 208 that can accommodate an endotracheal tube or LMA on either side of the Geudel airway. This can allow Geudel airway 200 to more easily sit directly adjacent to an endotracheal tube or LMA tube when the Geudel airway end opposite flange 206 is inserted into a patient's mouth and throat during surgery. The purpose of Geudel airway 200 is to remove gas that has leaked from, for example, an endotracheal tube or LMA seal that is also positioned in a patient's throat. The Geudel airway 200 can be attached to any suitable vacuum source to provide the desired suction. FIG. 7 illustrates an example of an adapter 210, which fits onto the Guedel airway and allows a user to easily attach an operating room vacuum source to the airway using a standard suction tube, such as conduit 108 in FIG. 1. For example, the adapter end 212 can be designed to be inserted into hole 204 at the flanged end of the Guedel airway to form an air-tight seal. Adaptor end 216 can be attached to the vacuum source. As oxygen and/or anesthetic are administered to the patient through the endotracheal tube or LMA, the vacuum source can suction any leaking gases through the vents 202 and hole 205 and into the Geudel airway 200. In an embodiment, the Guedel airway 200 can be used in place of the vented sleeve 100 in the system of FIG. 1.

Figure 9:
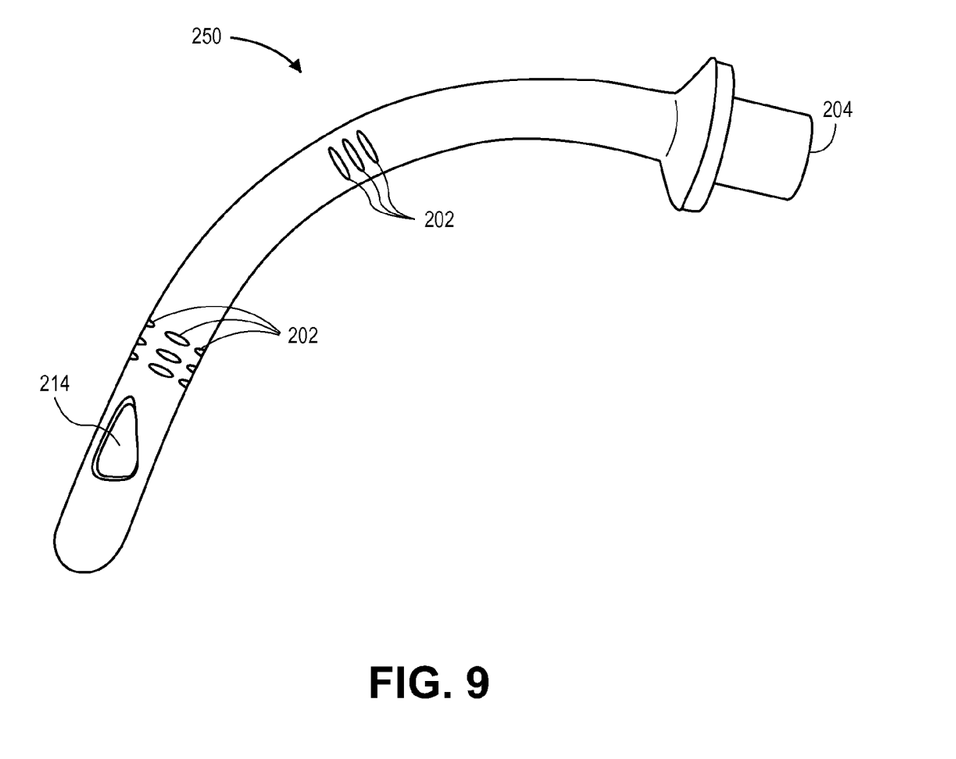
FIG. 9 illustrates a nasal trumpet device configured to collect gas from a patient, according to an embodiment of the present disclosure.

Other embodiments may exist that serve to provide this same functionality and these same concepts may be applied to other devices that are used to assist patients in need of breathing assistance, such as nasal trumpets. For example, FIG. 9 illustrates a nasal trumpet 250 comprising holes 204, 214 for the main air flow, as well as vents 202, similar to the Geudel airway design, according to an embodiment of the present disclosure. If desired, the vents 202 can be placed in multiple positions along the nasal trumpet to increase the amount of captured gases from the patient and/or to reduce the chance of air flow blockage through the device. An adapter, such as adapter 210 of FIG. 7, can be used to provide a connection between the hole 204 of nasal trumpet 250 and the vacuum source. In an embodiment, the nasal trumpet 250 can be used in place of or in addition to the vented sleeve 100 in the system of FIG. 1. The nasal trumpet 250 is placed through the patient's nares, in addition to, or instead of using the traditional mouth area for access. If desired, a pH detection system as desired herein above can be used in combination with any of the airway devices of the present disclosure, including the nasal trumpet 250, Guedel airway 200, sleeve 100, nasal tube 150 or endotracheal tube devices of FIG. 1 or 4.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

While the present teachings have been illustrated with respect to one or more implementations, alterations and/or modifications can be made to the illustrated examples without departing from the spirit and scope of the appended claims. In addition, while a particular feature of the present teachings may have been disclosed with respect to only one of several implementations, such feature may be combined with one or more other features of the other implementations as may be desired and advantageous for any given or particular function. Furthermore, to the extent that the terms "including," "includes," "having," "has," "with," or variants thereof are used in either the detailed description and the claims, such terms are intended to be inclusive in a manner similar to the term "comprising." Further, in the discussion and claims herein, the term "about" indicates that the value listed may be somewhat altered, as long as the alteration does not result in nonconformance of the process or structure to the illustrated embodiment. Finally, "exemplary" indicates the description is used as an example, rather than implying that it is an ideal.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompasses by the following claims.

What is claimed is:
1. A system for evacuating gas as it is leaking from a patient's airway, the system comprising:
an intubation device selected from an endotracheal tube or laryngeal mask airway, the intubation device comprising an airway tube and a primary seal positioned on an outer perimeter of the airway tube, the airway tube comprising a first flowpath configured to administer a gas to the patient, the primary seal configured to be positioned in the patient's airway to block a space between the airway tube and tissue lining the patient's airway;
a gas evacuation flowpath comprising one or more vents, the gas evacuation flowpath being separate from the first flowpath and configured to be inserted into the patient so that the one or more vents are positioned in the patient's mouth, the one or more vents being configured so that if a gas flow leaks past the primary seal, the gas flow is collected through the one or more vents;
a plug through which the intubation device extends, the plug comprising a material suitable for providing a secondary seal that is separate from the primary seal, wherein the gas evacuation flowpath comprising the one or more vents extends through the plug;

a vacuum source connected to the gas evacuation flowpath; and at least one sensor fluidly connected to the gas evacuation flowpath for determining the gas flow volume of any gas leaking past the primary seal or for determining a concentration of a measured gas in the gas flow.

2. The system of claim 1, wherein the at least one sensor is capable of real time, continuous monitoring of the gas flow that is evacuated from the patient.

3. The system of claim 2, further comprising:

a gas monitoring device in communication with the at least one sensor, the gas monitoring device including a component chosen from a data logger, alarm system or monitoring screen;

a vacuum pressure valve capable of providing a vacuum to the gas evacuation flowpath when it is placed inside the patient's airway; and a connection from the vacuum pressure valve to the vacuum source.

4. The system of claim 3, wherein the at least one sensor is configured to monitor at least one of oxygen concentration, anesthesia concentration, $CO_2$ concentration or pH.

5. The system of claim 1, wherein the plug is configured to expand to fill the patient's mouth cavity to provide the secondary seal.

6. A system for evacuating gas as it is leaking from a patient's airway, the system comprising:

an intubation device selected from an endotracheal tube or laryngeal mask airway, the intubation device comprising an airway tube and a primary seal positioned on an outer perimeter of the airway tube, the airway tube comprising a first flowpath configured to administer a gas to the patient, the primary seal configured to be positioned in the patient's airway to block a space between the airway tube and tissue lining the patient's airway;

a gas evacuation flowpath comprising one or more vents, the gas evacuation flowpath being separate from the first flowpath and configured to be inserted into the patient so that the one or more vents are positioned so that if a gas flow leaks past the primary seal, the gas flow is collected through the one or more vents;

a plug through which the intubation device extends, the plug comprising a material suitable for providing a secondary seal that is separate from the primary seal, wherein the gas evacuation flowpath comprising the one or more vents extends through the plug;

a vacuum source connected to the gas evacuation flowpath; and at least one sensor fluidly connected to the gas evacuation flowpath for determining the gas flow volume of any gas leaking past the primary seal or for determining a concentration of a measured gas in the gas flow.

7. The system of claim 6, wherein the first flowpath and the gas evacuation flowpath are both integrated into a multi-lumen endotracheal tube, the multi-lumen endotracheal tube comprising a first lumen and one or more smaller lumens, the first lumen being the first flowpath; and the one or more smaller lumens being the gas evacuation flowpath.

8. The system of claim 6, wherein the intubation device is a multi-lumen endotracheal tube comprising:

a first lumen configured to deliver anesthetic gases into and out of the lungs of the patient;

one or more outer lumens dedicated to providing vacuum pressure to evacuate gases that have leaked past the primary seal, the one or more outer lumens configured concentrically around the first lumen; and wherein the one or more vents are in fluid connection with the one or more outer lumens, the vents configured to collect gases that leak past the primary seal.

9. The system of claim 8, wherein the plug is positioned on the multi-lumen endotracheal tube, the vents being positioned between the primary seal and the plug.

10. The system of claim 9, wherein the plug comprises foam.

11. The system of claim 10, wherein the plug comprises open cell foam.

12. The system of claim 6, further comprising a plug through which the intubation device extends, the plug configured to provide a secondary seal in the patient's mouth that is separate from the primary seal.

13. A system for evacuating gas as it is leaking from a patient's airway, the system comprising:

an intubation device selected from an endotracheal tube or laryngeal mask airway, the intubation device comprising an airway tube and a primary seal positioned on an outer perimeter of the airway tube, the airway tube comprising a first flowpath configured to administer a gas to the patient, the primary seal configured to be positioned in the patient's airway to block a space between the airway tube and tissue lining the patient's airway;

a plug through which the intubation device extends, the plug being separate from the primary seal and configured to be positioned in the patient's mouth, the plug comprising one or more vents positioned therein;

a gas evacuation flowpath that is attached to or extends through the plug, the gas evacuation flowpath being separate from the first flowpath and configured to be inserted into the patient so that if a gas flow leaks past the primary seal, the gas flow can be evacuated from the patient; and a vacuum source connected to the gas evacuation flowpath; and at least one sensor fluidly connected to the gas evacuation flowpath for determining the gas flow volume of any gas leaking past the primary seal or for determining a concentration of a measured gas in the gas flow.

14. The system of claim 6, wherein the at least one sensor is configured to monitor at least one of oxygen concentration, anesthesia concentration, $CO_2$ concentration or pH.

* * * * *